United States Patent
Bronstein et al.

(10) Patent No.: US 6,686,171 B2
(45) Date of Patent: *Feb. 3, 2004

(54) COMPETITIVE CHEMILUMINESCENT ASSAY FOR CYCLIC NUCLEOTIDE MONOPHOSPHATES

(75) Inventors: Irena Y. Bronstein, Newton, MA (US); Anthony C. Chiulli, Maynard, MA (US); Michelle A. J. Palmer, Arlington, MA (US); John C. Voyta, Sudbury, MA (US)

(73) Assignee: Tropix, Inc., Bedford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/307,797

(22) Filed: May 10, 1999

(65) Prior Publication Data

US 2002/0115123 A1 Aug. 22, 2002

(51) Int. Cl.$^7$ .......................... A61K 51/00; G01N 33/53; G01N 33/542; G01N 33/537; G01N 33/543
(52) U.S. Cl. .......................... 435/7.93; 252/700; 435/7.1; 435/7.71; 435/7.72; 435/7.9; 435/7.91; 435/7.92; 435/7.93; 435/7.94; 435/21; 435/39; 435/69.3; 436/512; 436/513
(58) Field of Search .......................... 252/700; 362/34; 424/1.73; 435/7.1, 7.71, 7.72, 7.9, 7.91, 7.92, 7.93, 7.94, 7.95, 21, 39, 69.3; 436/512, 513; 935/81

(56) References Cited

U.S. PATENT DOCUMENTS

| | | | | |
|---|---|---|---|---|
| 4,115,538 A | * | 9/1978 | Satoh et al. | 424/1 |
| 5,089,424 A | * | 2/1992 | Khalil et al. | 436/518 |
| 5,145,772 A | * | 9/1992 | Voyta et al. | 435/4 |
| 5,399,500 A | * | 3/1995 | Oppenheimer et al. | 436/500 |
| 5,547,836 A | * | 8/1996 | Bronstein et al. | 435/6 |
| 5,654,154 A | * | 8/1997 | Bronstein et al. | 435/6 |
| 5,739,001 A | * | 4/1998 | Brown et al. | 435/7.93 |

OTHER PUBLICATIONS

Anthony C. Chiulli, et al., "A Novel High Throughput Chemiluminescent Assay for the Measurement of Cellular Cyclic Adenosine Monphosphate Levels", Journal of Biomolecular Screening, vol. 5, No. 4, (2000).

* cited by examiner

Primary Examiner—Lynette R. F. Smith
Assistant Examiner—JaNa Hines
(74) Attorney, Agent, or Firm—Piper Rudnick LLP; Steven B. Kelber (57) ABSTRACT

A competitive assay for the concentration of a cyclic nucleotide such as cyclic adenosine monophosphate combines, in a reaction chamber provided with a capture antibody, an antibody for the cAMP or other cyclic nucleotide, the sample to be assayed and a conjugate of cAMP and alkaline phosphatase. The mixture is incubated and washed, and after washing, a 1,2-dioxetane which is caused to decompose when contacted by the alkaline phosphatase of said conjugate is added. The light emission caused by decomposition is measured, with the strength of the signal being inversely related to the concentration of the cyclic nucleotide. Optionally, an enhancement agent in the form of a polymeric onium salt may be added, to further enhance the light emission.

28 Claims, 7 Drawing Sheets

COAT PLATES WITH GAR CAPTURE ANTIBODY
10 µg/ml, 200 µl/well
4°C, OVERNIGHT
↓
WASH
↓
BLOCK
350 µl/well
R.T., 1hr
↓
DRY
↓
SEAL, 2 PLATES/POUCH COAT PLATES WITH GAR CAPTURE ANTIBODY
10 μg/ml, 200 μl/well
4°C, OVERNIGHT

↓

WASH

↓

BLOCK
350 μl/well
R.T., 1hr

↓

DRY

↓

SEAL, 2 PLATES/POUCH

| VENDOR | TECHNOLOGY | NON-ACETYLATED | | ACETYLATED | |
|---|---|---|---|---|---|
| | | SENSITIVITY | DYNAMIC RANGE | SENSITIVITY | DYNAMIC RANGE |
| TROPIX | CL ELISA | 0.006 pmol | 0.006 TO 6000 pmol | NA | NA |
| AMERSHAM | SPA/RADIOACTIVITY | NA | 0.02 TO 1.8 pmol | NA | NA |
| NEN | FLASHPLATE/RADIOACTIVITY | NA | 0.5 TO 50 pmol | NA | 0.0025 TO 0.4 pmol |
| IGEN | ELECTROCHEMILUMINESCENCE | NA | 0.075 TO 19 pmol | NA | NA |
| ASSAY DESIGN | COLORIMETRIC ELISA | 0.038 pmol | 0.05 TO 500 pmol | 0.0175 pmol | 0.005 TO 50 pmol |
| PERSEPTIVE BIO. | FLUORESCENT ELISA | 0.001 pmol | 0.0025 TO 5 pmol | 0.001 pmol | 0.0005 TO 1 pmol |

COMPETITIVE CHEMILUMINESCENT ASSAY FOR CYCLIC NUCLEOTIDE MONOPHOSPHATES

BACKGROUND OF THE INVENTION

1. Field of the Invention

This invention pertains to a competitive chemiluminescent assay for the detection of the presence of cyclic nucleotide monophosphates. In general, the cyclic nucleotide phosphates appear only as monophosphates, due to chemical structure considerations. Among these, cyclic adenosine monophosphate (camp) is perhaps the most widely known, implicated as a primary or secondary messenger in a variety of cellular, intracellular and extracellular pathways. This invention takes advantage of the high sensitivity of chemiluminescent 1,2-dioxetane reagents to overcome sensitivity and dynamic range problems encountered in the prior art.

2. Background of the Prior Art

A wide variety of metabolic responses are keyed to release of intracellular cAMP. In many cases, these responses are mediated by cAMP-dependent protein kinase which, in the presence of elevated cAMP levels, triggers a wide variety of activating reactions. Among the best known metabolic responses keyed to cAMP are the conversion of glycogen to glucose in the liver, as well as a variety of activities keyed to the glycogen/glucose energy cycle. The principle hormone in this cycle which induces a rise in cAMP is epinephrine. There are, however, a wide variety of other hormones which will also trigger cAMP release, which in turn keys a metabolic response mediated by the kinase. These include adrenocorticotropic hormone (ACTH), follicle-stimulating hormone (FSH), luteinizing hormone (LH). thyroid-stimulating hormone (TSH), parathyroid hormone, vasopressin and prostaglandin I. Accordingly, it is clear cAMP levels in specific tissues of mammals, including humans, may be key indicators of a variety of hormonal functions and interactions.

cAMP is only the best known of the cyclic nucleotides. In general, cyclic nucleotides appear as monophosphates. Guanosine monophosphate (cGMP), uridine monophosphate (cUMP) and cytidine monophosphate (cCMP) may all importantly bear on a wide variety of hormonal functions and intercellular interactions, that may be desirably measured. cAMP is the most studied of these "messenger" cyclic nucleotides.

Assays, including competitive ELISA assays, for cAMP are known. A widely reported assay is available from Assay Design, and is a colorometric assay. Other immunoassay products are available from Amersham Med-Physics, Inc. (a radioimmunoassay) as well as IGEN and NEN. The Assay Design embodiment employs assay kits (also available under the mark Biomol® in a classic example of a competitive ELISA assay, in which the strength of the signal is inversely proportional to the concentration of the cyclic nucleotide present. The kit from Biomol is for measurement of light absorption. A fluorescent assay kit is available from Perseptive Biosystems.

Because of the very low values of cyclic nucleotides that may need to be detected in a variety of tissue samples, high sensitivity is required. Many of the commercially available assays for cAMP itself do not offer this sensitivity, and require acetylation of the cAMP (to promote better antibody binding) for greater sensitivity.

Accordingly, it remains a goal of those of skill in the art to find a competitive immunoassay which is highly sensitive, offers a broad dynamic range, and employs reagents which can be obtained through simplified procedures, including avoidance of acetylation.

SUMMARY OF THE INVENTION

The above objects, and others discussed in more detail below, are met by a chemiluminescent competitive ELISA assay which relies on the high chemiluminescent sensitivity of 1,2-dioxetanes. These dioxetanes, developed by the common assignee herein, Tropix, Inc., a division of P.E. Biosystems, are the subject of a wide variety of United States patents. The 1,2-dioxetanes that are useful in the claimed invention typically have a generic structure of Formula I:

(I)

In Formula I, $Y_1$, $Y_2$ and X are variously electron-active moieties, in that they are either electron donating or electron withdrawing. Exemplary groups include halogens, particularly chlorine, alkoxies, particularly methoxy, amine, alkyl, etc. In the alternative, these groups are hydrogen. Any one or more of $Y_1$, $Y_2$ or X may be other than hydrogen, or they may all be hydrogen. Substituent R is an alkyl, aralkyl, cyclic alkyl, heteroalkyl comprising an O, N, P or S moiety, in general of less than 20 carbon atoms. Desirably, R is alkyl. R may be substituted with groups intended to enhance solubility as well as reactivity, which may include halogen substituents such as one or more fluorine atoms, carboxy (COO) substituents, sulfoxy substituents, etc. The same substituents to enhance solubility may also be present on $Y_1$, $Y_2$ or X. Ar is an aryl moiety, typically phenyl or naphthyl, most preferably phenyl. Z is a moiety which includes a bond which is cleaved by an enzyme, which, when cleaved, leaves either O or N attached to the aryl moiety. This anion destabilizes the dioxetane, leading to its decomposition. On decomposition, the dioxetane releases light. For the purposes of this invention, Z is a phosphate moiety, preferably disodium phosphate. Dioxetanes of this type are disclosed in U.S. Pat. Nos. 4,962,192; 4,931,569; 5,112,960; 5,145,772 and 5,654,154, as well as a variety of others. All of the foregoing patents are incorporated herein by reference. As disclosed, e.g., in U.S. Pat. No. 5,112,960, an enzyme-triggerable dioxetane such as 3-(4-methoxyspiro [1,2-dioxetane-3,2'-tricyclo[3.3.1.1$^{3,7}$] decan-4-phenylphosphate and its salts (AMPPD) is a highly effective reporter molecule of this type. Derivitisation of this "unsubstituted" 1,2-dioxetane with substituents on the adamantyl ring, such as a chlorine atom (CSPD) can dramatically improve performance. Similarly, substituents on the phenyl ring besides the enzyme-cleavable substituent, particularly at the 3 or meta position, give further improved yields. These reporter molecules, which are chemiluminescent in nature, are referred to as enzyme-triggerable dioxetanes. The particular enzyme acting in the claimed invention is alkaline phosphotase, selecting therefore, Z as a phosphate moiety.

As set forth in U.S. Pat. No. 5,145,772 and 5,336,595, also incorporated herein by reference, the use of polymeric onium salts (ammonium, phosphonium and sulfonium) as enhancer molecules results in a heightened degree of light emission from the dioxetane on decomposition. This is due to the tendency of these macromolecular polymers to sequester the dioxetane anion, which is highly hydrophobic in non-aqueous "micro environments", which maximizes chemiluminescent emission. As further disclosed in U.S. Pat. No. 5,145,772, these dioxetanes may be combined with energy accepting fluorescent molecules, such as fluorescein, such that the energy released by the dioxetane on decomposition is transferred to the fluorescent receiver, the fluorescence being detected. The assay of this invention is particularly suited for chemiluminescent emission.

Neither the 1,2-dioxetanes, nor their preparation or use, per se, of enhancement agents, alone, or with secondary enhancement agents such as those taught in U.S. Pat. No. 5,547,836, constitute an aspect of the invention, per se.

In the assay of this invention, a microtiter well or similar "reaction chamber" is coated with a capture antibody, which is exemplified by goat anti-rabbit IgG (available from a wide variety of sources, including American Qualex).

According to the invention, a conjugate of cAMP and alkaline phosphatase is prepared and added to the well with an antibody for cAMP (or other cyclic nucleotide) and the sample to be inspected (or standard). The reaction mixture is incubated, and washed. Thereafter, an alkaline phosphatase-triggerable 1,2-dioxetane, such as CSPD, is added, preferably in the presence of an enhancer, such as poly (vinylbenzyltributyl ammonium chloride) or other enhancement agents. The dioxetane is incubated, and the reaction chamber inspected, preferably with a luminometer, or some other type of light-sensitive device, for chemiluminescent signal. The stronger the signal, the lower the cyclic nucleotide concentration in the sample.

DETAILED DESCRIPTION OF THE INVENTION

The assay protocol of this invention resembles other competitive immunoassays, and provides an inverse relationship between intensity of signal detected and cyclic nucleotide concentration. Although the invention is generically applicable to the cyclic nucleotides, including cAMP, cGMP, cCMP, cUMP, cIMP and cTMP, cAMP and cGMP, which frequently appear in a tandem, inverse relationship in a wide variety of biophysical pathways, receive the most attention. cAMP is clearly the most well studied and characterized of the cyclic nucleotides, and accordingly, this invention is exemplified using cAMP and cAMP detection reagents. The substitution of reagents, in particular, primary antibodies, preferably monoclonal antibodies, for the other cyclic nucleotides is straight forward and easily arrived at by one of skill in the art, given the disclosure herein.

This invention is also exemplified using CSPD, where, in the general Formula I given above, the adamantyl group is substituted with 1 chlorine atom, X is hydrogen, R is methyl and Z is phosphate. Other alkaline phosphatase-triggerable 1,2-dioxetanes corresponding to the general Formula I may be used in its place.

This invention is also exemplified using an enhancement agent, commercially available from Tropix, Inc. As an exemplary enhancement agent, poly (vinylbenzyltributylammonium chloride) is selected. An enhancement agent is preferred, but not required for the practice of the invention. Other quaternary onium polymers, as well as hydrophobic macromolecules such as large proteins, including bovine serum albumin, or mixtures thereof may be similarly employed.

Figure 1:
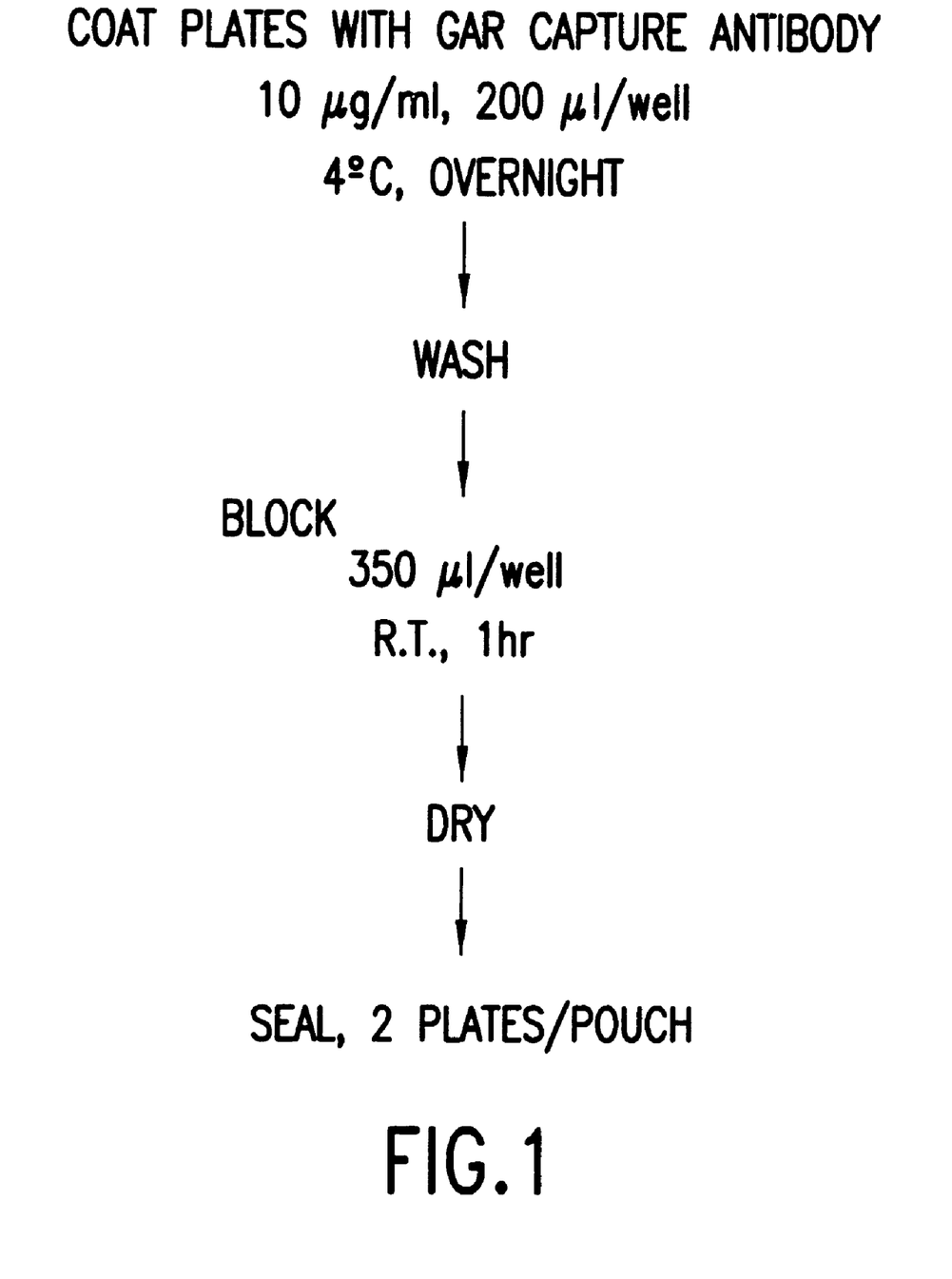
FIG. 1 is a flowchart illustration of the method of manufacturing coated plates or reaction chambers of the invention.

In the practice of the invention, the wells of conventional microtiter plates, or similar reaction chambers, are first coated with capture antibody. In the exemplification of this invention, the capture antibody is a goat anti-rabbit antibody. The wells of the plates are coated with a preparation of the capture antibody, incubated overnight, and then washed. To avoid non-specific binding, the rest of the plate may be treated, so as to suppress any interaction therewith. Accordingly, after washing, each plate is treated with SUPERBLOCK® blocking buffer (available from Pierce) or similar agent. The plate is thereafter dried. This process is reflected in FIG. 1.

The prepared plates are now ready to perform as reaction chambers, or wells, for the competitive assay. The source of cAMP is either standards prepared to specific dilutions, in order to establish standardized values, or cells that have been subjected to some type of stimulus, and are then lysed, so as to provide sample material for inspection. Thus, the cell lysate or cAMP standard is added to the wells, together with a conjugate of cAMP and alkaline phosphatase, described herein below. Final addition to the reaction mixture is the primary antibody, an antibody for cAMP. Both polyclonal and monoclonal antibodies are available against cAMP. Either may be used effectively. Rabbit anti-cAMP antibodies are available from Zymed Laboratories, Inc. as well Immunogen. Other antibodies are similarly available. The reactants are mixed in the coated well, and then incubated to insure adequate antibody binding. Typically, incubation is at room temperature for a period of about one hour. Subsequently, the incubated reaction mixture is washed repeatedly with a wash buffer which may be 0.05 M carbonate bicarbonate and 0.05% Tween-20 -surfactant, preferably polysorbate 20 (available from ICI Surfactants under the name TWEEN-20®). at a pH of about 8.0–11.0, an exemplary value being about 9.6. While Applicants do not wish to be bound by this theory, the alkaline character of the wash buffer may improve alkaline phosphatase performance. The assay buffer itself is BSA (0.02%) with sodium acetate (0.05 molar) at a pH convenient for the assay, between about 5.5 and 6.0, preferably about 5.8. Those of skill in the art will appreciate that the identities of the blocking buffer, the wash buffer and the assay buffer, as well as the buffer used to coat the microtiter wells, are not rigid features of the invention, per se, but rather can be varied by those of ordinary skill in the art and still employ the claimed invention.

After washing, the dioxetane, with the enhancer, if any, is added. A further incubation, to permit a glow discharge from the chemiluminescent dioxetane to reach a constant level, approximately 30 minutes at room temperature, follows, and then the chemiluminescent signal is read in a detection device, such as the (Tropix 717 ™ or North Star luminometer detection device (CCD)(North Star ™ HTS system) . The assay protocol itself is set forth in FIG. 2.

Figure 2:
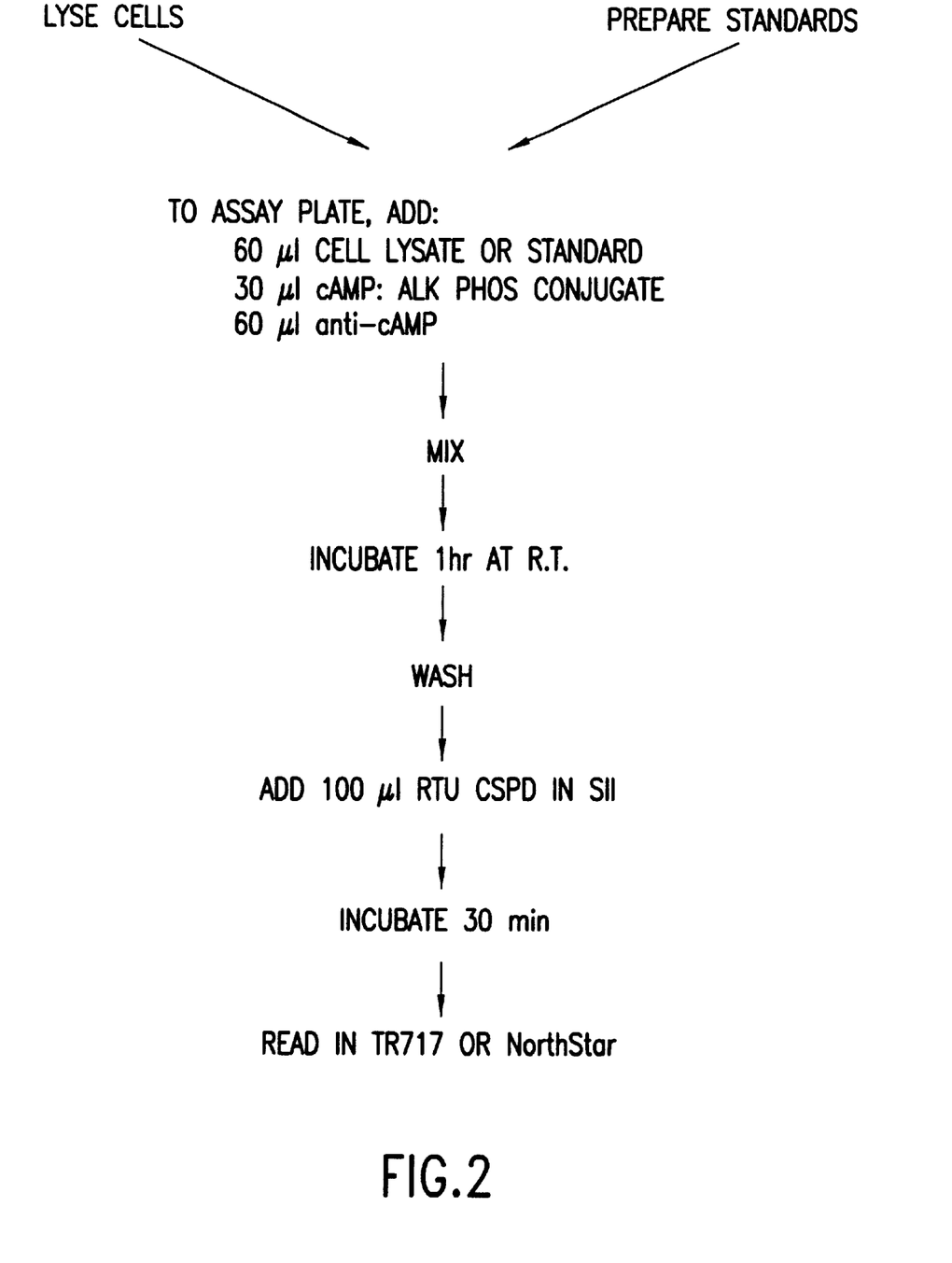
FIG. 2 is a flowchart illustration of the steps of the assay of the invention.
Figure 3:
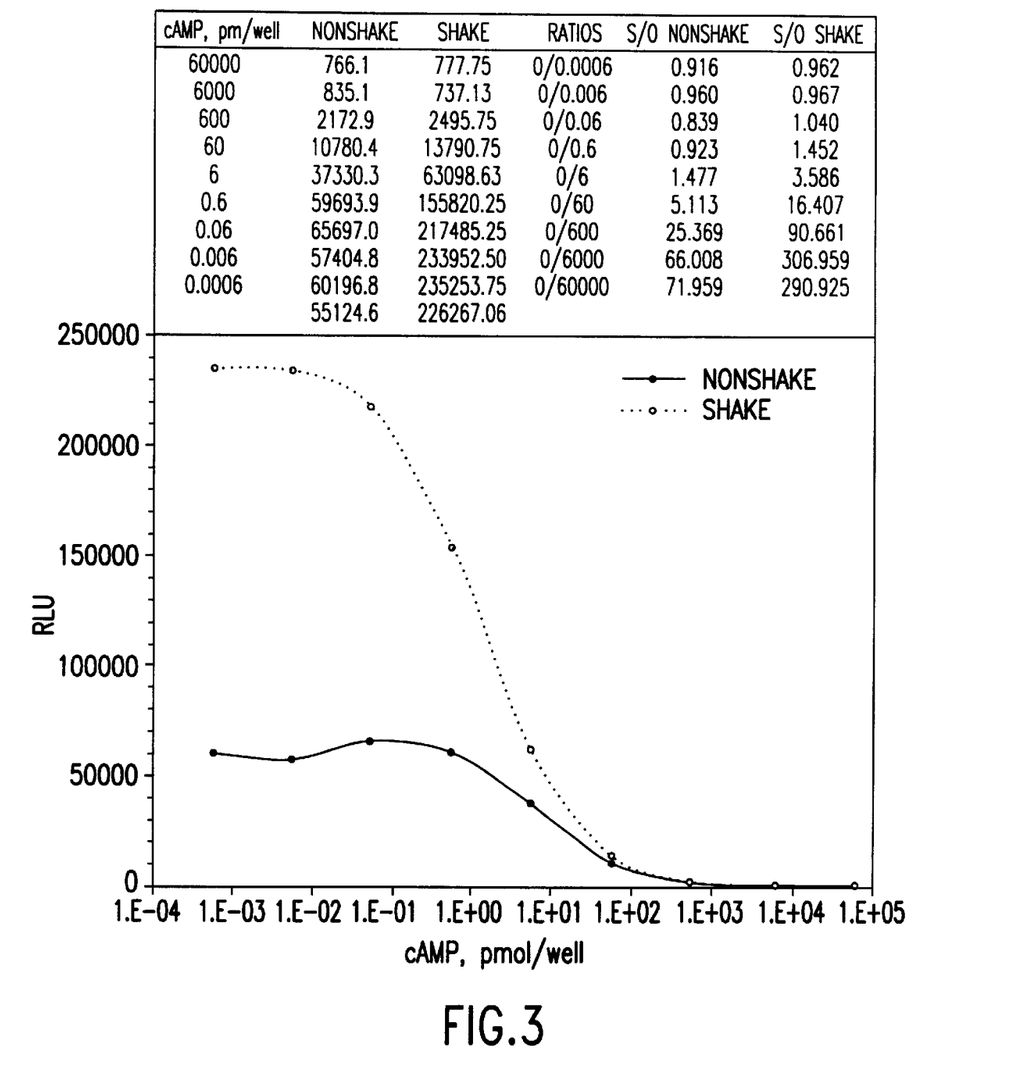
FIG. 3 provides graphic illustration and tabular data comparing the signal obtained by shaking the reaction mixture, as opposed to not shaking it, during the incubation period.

It is clear that the assay is optimized for automated robotic assay systems, providing high throughput opportunities. Incubation for one hour, as reflected in FIG. 2, is the standard protocol. Results, in terms of sensitivity and dynamic range, may significantly improve if the microtiter plates, or other reaction chambers, are shaken during the incubation period. The relative performance of shaken and non-shaken assays is reflected in FIG. 3 hereto.

This assay is suitable for use in a wide variety of conditions. The heightened sensitivity, and broadened dynamic range, makes application consistent with a wide variety of variables. When standards have been established, the samples assayed according to this invention can be obtained by lysing mammalian adherent and non-adherent cell lines. Optimal performance can be achieved across a wide range of cell densities, ranging from 1,000–100,000 cells per well, depending on cell type in a 96 -well plate. Other plates with a higher number of wells, may be used. The use of luminometers to detect the chemiluminescent signal (light emission) is recommended. If a luminometer is used, an appropriate measure is 1 second per well. In the alternative, a scintillation counter, such as that available under the trademark Top Count @ may be used as a substitute for a luminometer. Sensitivity may be reduced, and it is necessary to turn off the coincident circuit to measure chemiluminescence directly.

Figure 4:
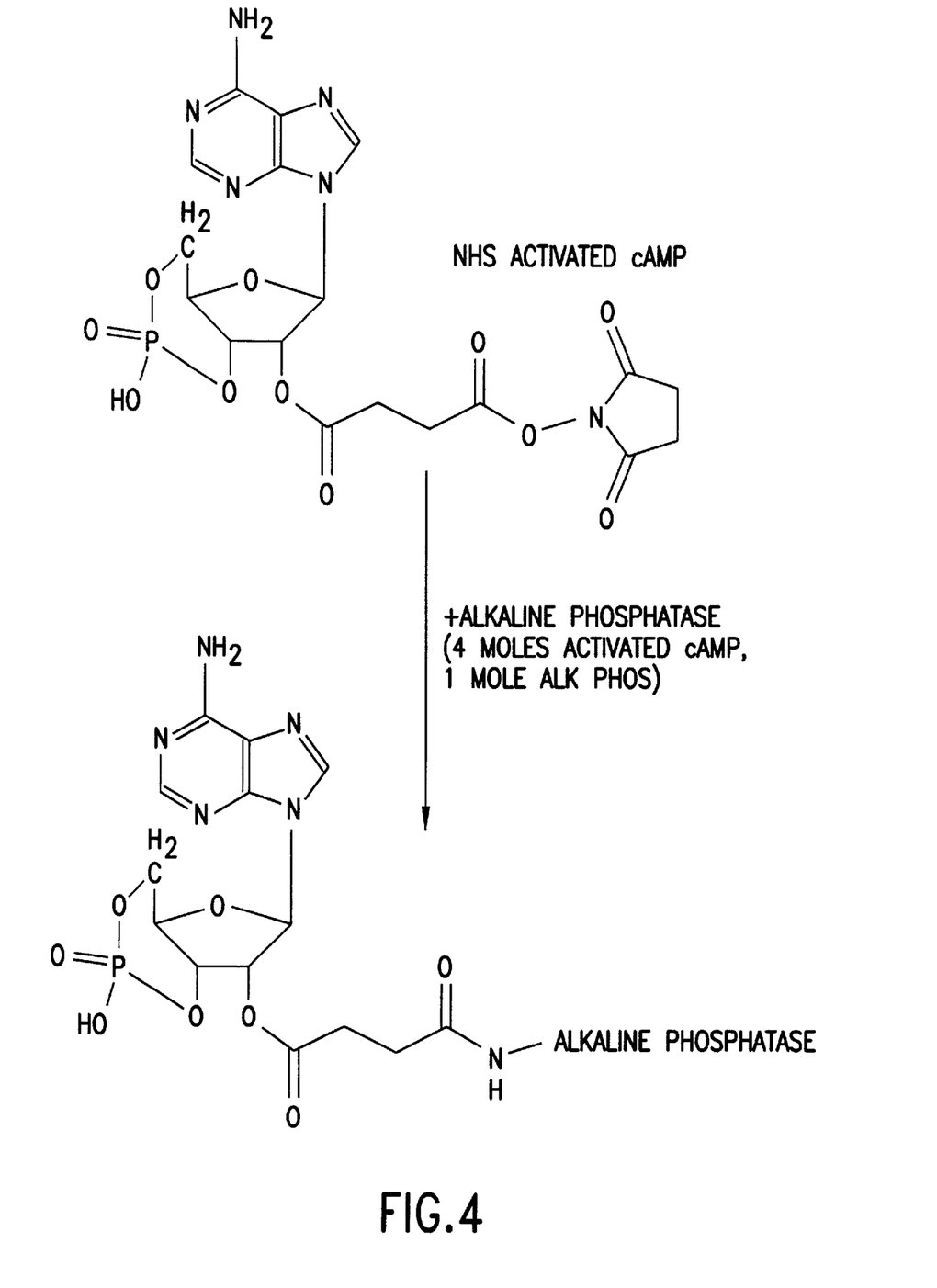
FIG. 4 is a schematic illustration of the formation of the alkaline phosphatase/cyclic nucleotide conjugate of the invention.

The "competitive" basis of the assay is the use of a conjugate of cAMP and alkaline phosphatase (cAMP-AP conjugate).to compete with the cAMP in the sample for antibody. It is the alkaline phosphatase of this cAMP-AP conjugate, captured by the antibody specific for cAMP, that cleaves the alkaline phosphatase-cleavable dioxetane. Thus, the lower the cAMP concentration in the lysed sample, the more cAMP-AP conjugate is captured by the primary antibody, and the larger the signal. Preparation of the conjugate is straight forward, and comprises combining NHS activated cAMP with alkaline phosphatase (in a ratio of 4 moles activated cAMP to 1 mole AP). This preparation is reflected in FIG. 4.

Figure 5:
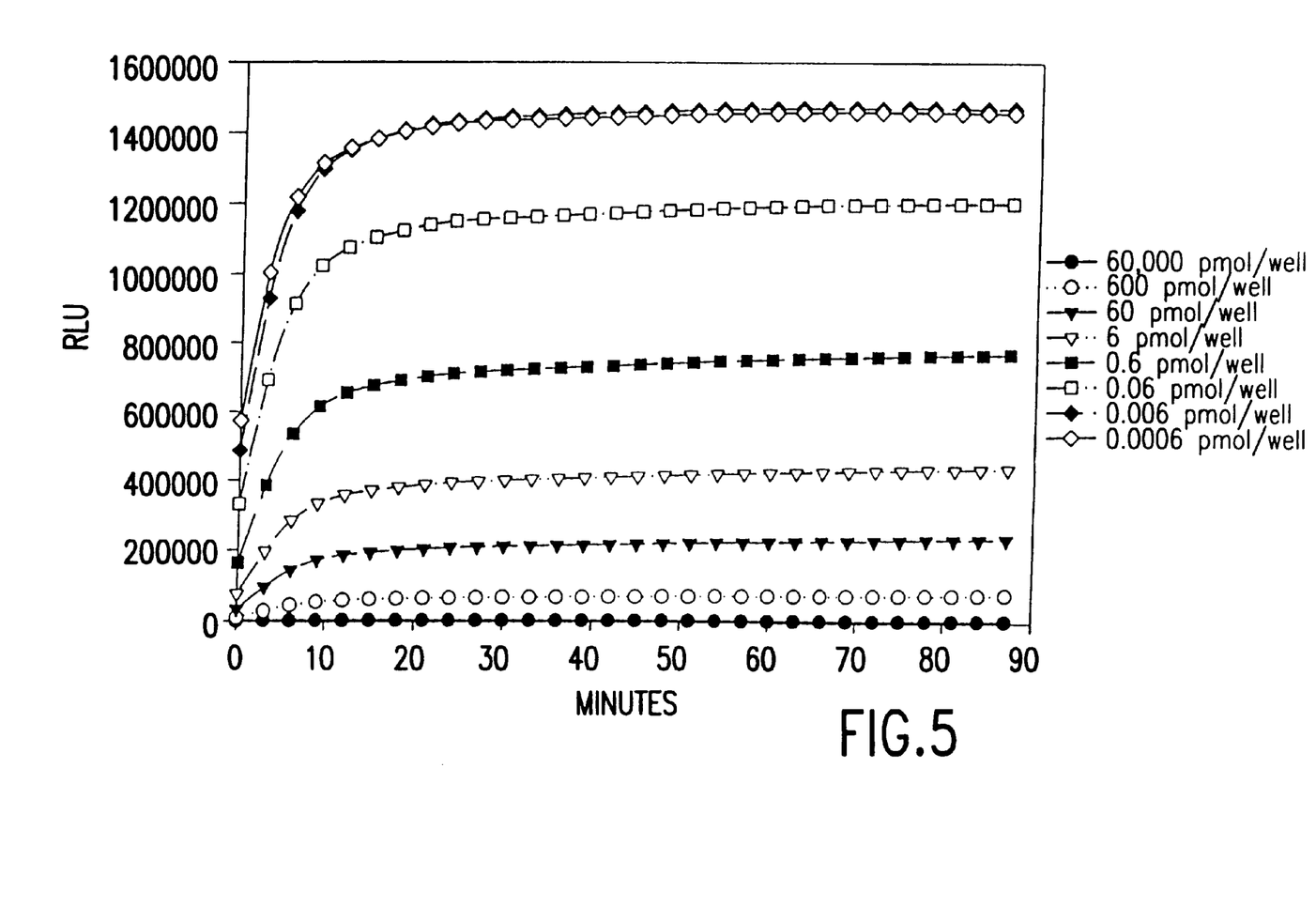
FIG. 5 is a graphic illustration of standardized signals vs. time for a variety of concentration of cAMP.

As noted above, it is necessary to establish standards, so that actual concentrations in lysed samples can be determined, on the basis of established concentration. A typical standard curve collection is reflected in FIG. 5, which shows the superior performance of this assay.

Figure 6:
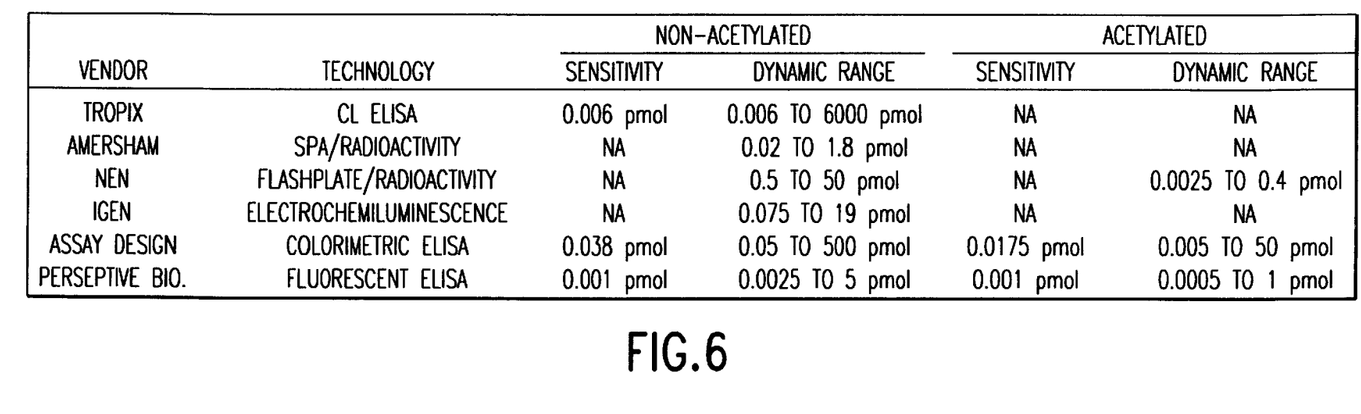
FIG. 6 is a table comparing sensitivity and dynamic range of the claimed invention compared with other commerical assays for cAMP.

Sensitivity and dynamic range for a variety of cAMP detection assays have been published. Sensitivity and dynamic range of a variety of detection systems are set forth in FIG. 6. It is clear that the unexpected improvements in sensitivity and dynamic range obtained by combining dioxetane chemiluminescent technology with cAMP-specific immunoassay techniques has led to an unexpectedly superior performance, even in the absence of acetylation.

Figure 7:
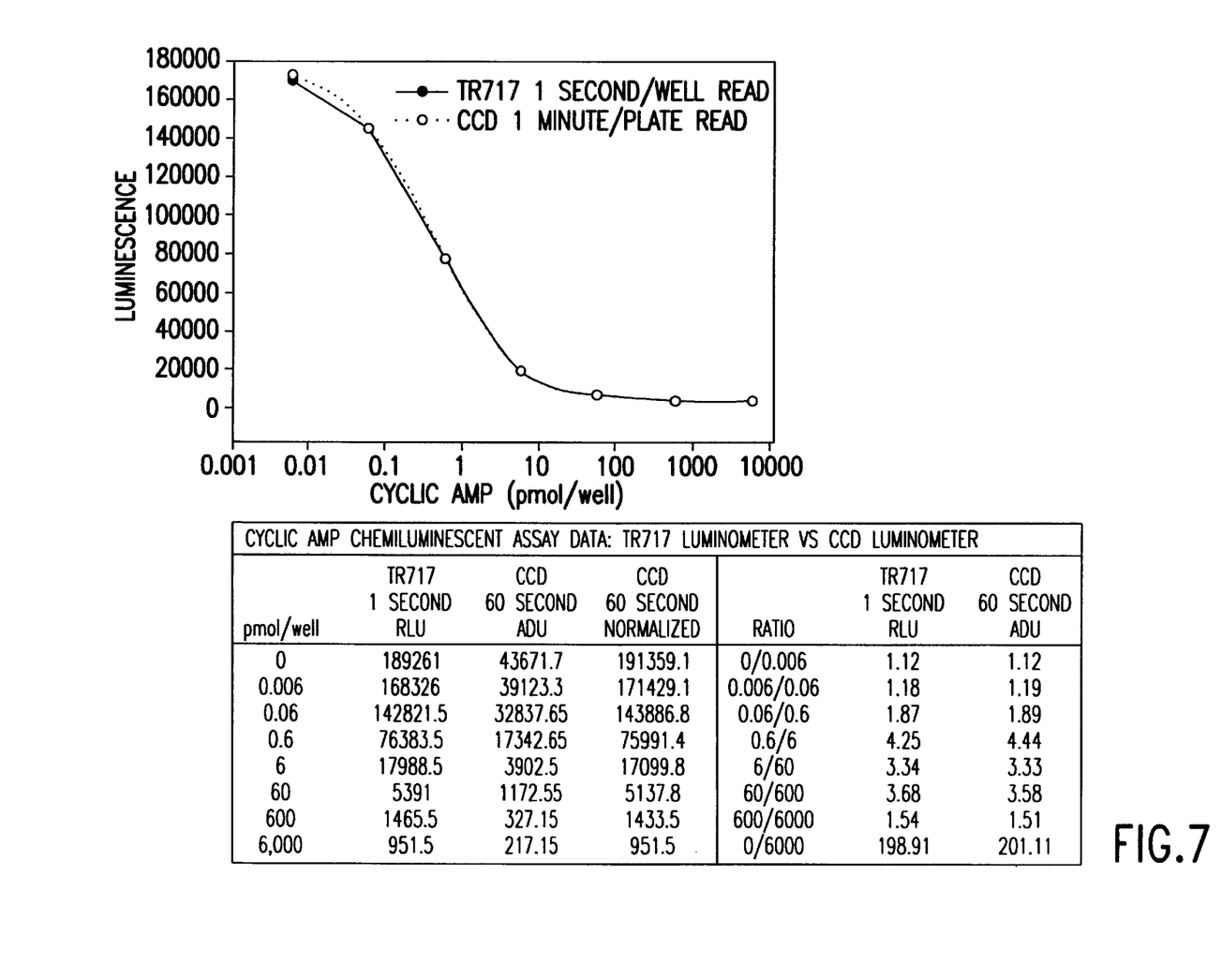
FIG. 7 compares the data obtained from two different luminometers according to the invention of this application.

As previously noted, the cyclic AMP chemiluminescent assay of the invention is preferably detected by the luminometer. Two exemplary luminometers are compared in FIG. 7, TR717™ verses Northstar ™ HTS system. Both give the improved performance advantageously provided by this invention.

This invention has been disclosed generically, and in terms of specific examples. The specific examples are not intended, and should not be construed, as limiting, unless so indicated. In particular, variations in the identity of the dioxetane, buffer compositions, signal detecting apparatus, protocol time, temperatures and conditions and the like will occur to those of ordinary skill in the art without the exercise of inventive faculty. Unless excluded by the recitation of the claims set forth below, these variations remain within the scope of the invention.

What is claimed is:

1. A competitive assay for determining the concentration of a cyclic nucleotide phosphate in a sample comprising cells, the assay comprising:

lysing cells in the sample;

combining, in a reaction chamber provided with a capture antibody, (1) a conjugate of said cyclic nucleotide phosphate and an alkaline phosphatase, (2) a primary antibody that is bound by said capture antibody and that binds, when so bound, said cyclic nucleotide phosphate, and (3) said sample to form a reaction mixture and incubating the reaction mixture so as to permit binding of said primary antibody and said conjugate, washing said reaction mixture to remove any unbound conjugate or antibody, adding to said reaction mixture an alkaline phosphatase-triggered 1,2-dioxetane which, when contacted with alkaline phosphatase in said conjugate, is caused to decompose and release light, and detecting any chemiluminescent signal emitted by said reaction mixture, wherein said signal is indicative of the concentration of cyclic nucleotide phosphate in the sample.

2. The method of claim 1, wherein said capture antibody is provided on the surface of a reaction chamber.

3. The method of claim 2, wherein said reaction chamber is a well of a microtiter plate.

4. The method of claim 1, wherein a polymeric onium salt enhancer is added with said dioxetane, so as to enhance the amount of light emitted by said dioxetane when triggered, in comparison with the amount of light emitted in the absence of said enhancer.

5. The method of claim 1, wherein said chemiluminescent signal is detected by a luminometer.

6. The method of claim 1, wherein said reaction mixture is shaken at least once after said 1,2-dioxetane is added to said reaction mixture.

7. The method of claim 3, wherein those portions of the walls of said microtiter plate not provided with said capture antibody are blocked from reaction with the components of the reaction mixture.

8. The method of claim 1, wherein said cyclic nucleotide phosphate is cyclic adenosine monophosphate (cAMP), cyclic guanosine monophosphate (cGMP), cyclic uridine monophosphate (cUMP) or cyclic cytidine monophosphate (cCMP).

9. The method of claim 1, wherein said cyclic nucleotide phosphate is cAMP.

10. A kit for conducting a competitive, cell-based immunoassay for the concentration of a cyclic nucleotide phosphate, said kit comprising:

a conjugate of said cyclic nucleotide phosphate and an alkaline phosphatase;

an antibody which binds said cyclic nucleotide phosphate; and an alkaline phosphatase-triggered 1,2-dioxetane which decomposes in the presence of alkaline phosphatase to release light.

11. The kit of claim 10, wherein said kit further comprises a polymeric onium salt which enhances the amount of light release in an assay conducted with said kit by decomposition of said dioxetane, as compared with the amount of light emitted in the absence of said polymeric onium salt.

12. The kit of claim 10, wherein said kit further comprises a reaction chamber.

13. The kit of claim 12, wherein portions of said reaction chamber is coated with a capture antibody.

14. The kit of claim 13, wherein the portions of said reaction chamber that are not coated with the capture antibody which, when the assay is performed, come in contact with a reagent are blocked from reacting with reagents.

15. The kit of claim 10, wherein said antibody which binds said cyclic nucleotide phosphate is a monoclonal antibody.

16. The kit of claim 15, wherein said cyclic nucleotide phosphate is cAMP, cGMP, cUMP or cCMP.

17. The kit of claim 16, wherein said cyclic nucleotide phosphate is cAMP.

18. The method of claim 1, wherein said washing step is performed with a buffer of pH 8.0–11.0.

19. The method of claim 18, wherein said washing step buffer is comprised of carbonate bicarbonate and surfactant.

20. The assay of claim 1, wherein the cyclic nucleotide phosphate is not acetylated.

21. The method of claim 20, wherein the assay has a sensitivity as low as 0.006 pmol.

22. The method of claim 20, wherein the assay has a dynamic range of up to five logs.

23. The assay of claim 1, wherein the cells are lysed before the sample is added to the reaction chamber.

24. The assay of claim 1, wherein the cells are lysed after the sample is added to the reaction chamber.

25. A competitive assay for determining the concentration of a cyclic nucleotide phosphate in a sample comprising cells, the assay comprising:

lysing cells in the sample;

combining, in a reaction chamber provided with a capture antibody, (1) a conjugate of said cyclic nucleotide phosphate and an alkaline phosphatase, (2) a primary antibody that is bound by said capture antibody and that binds, when so bound, said cyclic nucleotide phosphate, and (3) said sample to form a reaction mixture, incubating the reaction mixture so as to permit said cyclic nucleotide phosphate and said conjugate to bind competitively with said primary antibody, washing said reaction mixture to remove any unbound conjugate or antibody, adding to said reaction mixture an alkaline phosphatase-triggered 1,2-dioxetane which, when contacted with alkaline phosphatase in said conjugate, is caused to decompose and release light, and detecting any chemiluminescent signal emitted by said reaction mixture, wherein said signal is indicative of the concentration of cyclic nucleotide phosphate in the sample.

26. The assay of claim 25, wherein the cells are lysed before the sample is added to the reaction chamber.

27. The assay of claim 25, wherein the cells are lysed after the sample is added to the reaction chamber.

28. The assay of claim 25, wherein the cyclic nucleotide phosphate is not acetylated.

* * * * *